United States Patent [19]

Kramer et al.

[11] 3,949,080

[45] Apr. 6, 1976

[54] COMPOSITIONS CONTAINING O,N-ACETAL AND METHOD OF USING SAME

[75] Inventors: Wolfgang Kramer; Karl Heinz Buchel; Werner Meiser; Manfred Plempel, all of Wuppertal, Germany

[73] Assignee: Bayer Aktiengesellschaft, Germany

[22] Filed: Apr. 30, 1974

[21] Appl. No.: 465,617

[30] Foreign Application Priority Data
May 15, 1973 Germany............................ 2324424

[52] U.S. Cl. ............................................... 424/269
[51] Int. Cl.$^2$........................................ A61K 31/41
[58] Field of Search..................................... 424/269

[56] References Cited
UNITED STATES PATENTS

| | | | |
|---|---|---|---|
| 3,723,622 | 3/1973 | Buchel et al. | 424/269 |
| 3,755,349 | 8/1973 | Timmler et al. | 424/269 |
| 3,769,411 | 10/1973 | Seidel et al. | 424/269 |
| 3,812,142 | 5/1974 | Meiser et al. | 424/269 |

*Primary Examiner*—Jerome D. Goldberg

[57] ABSTRACT

Pharmaceutical compositions comprising a triazolyl-O,N-acetal as the active ingredient and method of using same. The said compositions are useful as antimicrobials and are especially useful as antimycotic agents.

39 Claims, No Drawings

COMPOSITIONS CONTAINING O,N-ACETAL AND METHOD OF USING SAME

This invention relates to new pharmaceutical compositions and to a method of using same.

Specifically this invention relates to new pharmaceutical compositions in which the active ingredient is a triazolyl-O,N-acetal or a salt thereof which have utility as antimicrobials and more particularly as antimycotic agents.

The active ingredient in the instant compositions is a triazolyl-O,N-acetal of the following formula:

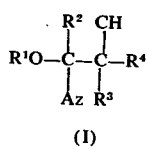

(I)

wherein
R¹ is alkyl, alkenyl, alkynyl, cycloalkyl, cycloalkenyl, aryl, substituted aryl, aralkyl or substituted aralkyl;
R², R³ and R⁴ are the same or different radicals selected from hydrogen, alkyl, alkenyl, alkynyl, cycloalkyl, cycloalkenyl, aryl, substituted aryl, aralkyl or substituted aralkyl with the proviso that R³ and R⁴ cannot both be hydrogen at the same time;
Az is 1,2,4-triazol-1-yl, 1,2,4-triazol-4-yl, 1,2,3-triazol-1-yl and mono- and disubstituted derivatives thereof in which the substituents are selected from halo and lower alkyl.

The term alkyl in the preceding definition of R¹, R², R³ and R⁴ includes straight or branched chain alkyl of 1 to 6 carbon atoms and, preferably, straight or branched chain lower alkyl of 1 to 4 carbon atoms such as methyl, ethyl, n-butyl and t-butyl. Especially preferred among the R² lower alkyl groups is methyl and especially preferred among the R⁴ lower alkyl groups are methyl and t-butyl.

The terms alkenyl and alkynyl in the definition of R¹, R², R³ and R⁴ include the straight and branched chain alkenyl and alkynyl groups of 2 to 6 carbon atoms and, preferably, alkenyl and alkynyl of 3 to 6 carbon atoms. Illustrative of these substituents are, for example, allyl, propargyl, butin-(2)-yl, butin-(3)-yl, pentin-(3)-yl and pentin-(4)-yl.

The terms cycloalkyl and cycloalkenyl in the definition of R¹, R², R³ and R⁴ refer to cycloaliphatic substituents of 5 to 7 carbon atoms and, preferably, 5 or 6 carbons. Illustrative of these substituents are, for example, cyclohexyl, cyclopentyl, cyclohexen-(2)-yl, cyclohexen-(1)-yl, cyclohexen-(3)-yl, cyclohexen (4)-yl and cyclopenten-(2)-yl.

The term Az in formula I, supra, represents one of the following triazolyl radicals:

  

including the mono- and disubstituted derivatives thereof wherein one or both of the carbons in said triazolyl nuclei may be substituted by halo or lower alkyl. Typical of said mono- and disubstituted triazolyls are the following:

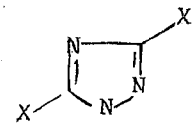

wherein the two X radicals are similar or dissimilar members selected from hydrogen, halo such as chloro, bromo, fluoro or iodo but, preferably, chloro or bromo or a lower alkyl of 1 to 4 carbon atoms, such as methyl, ethyl, n-propyl, isopropyl, n-butyl, isobutyl or t-butyl but, preferably, methyl. Especially preferred among these substituted triazolyl groups are the following:

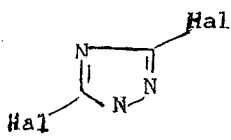 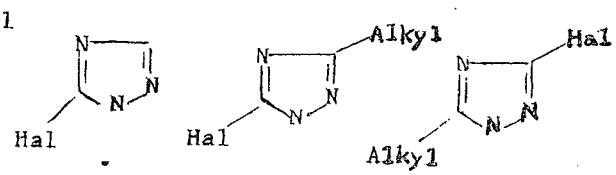

wherein Hal represents halo, preferably, chloro or bromo, and Alkyl represents lower alkyl of 1 to 4 carbon atoms such as methyl, ethyl, n-propyl, isopropyl, n-butyl, isobutyl and t-butyl but, preferably, methyl.

A preferred embodiment of this invention comprises those pharmaceutical compositions containing as the active ingredient a triazolyl-O,N-acetal wherein the triazolyl nucleus is unsubstituted.

The terms aryl and aralkyl in the definition of R¹, R², R³ and R⁴ include mono- and binuclear aromatic moieties of 6 to 10 carbon atoms as, for example, phenyl, naphthyl, benzyl or phenethyl. Optionally, the said aryl and aralkyl moieties may be substituted at a nuclear carbon by 1 to 4 substituents, preferably, 1 to 3 substituents and, more preferably, 1 or 2 substituents. These substituents include:

lower alkyl of the straight chain or branched chain variety containing 1 to 4 carbon atoms as, for example, methyl, ethyl, n-propyl, isopropyl, n-butyl, isobutyl and t-butyl;

halo as, for example, fluoro, chloro and bromo;

halo lower alkyl of 1 or 2 carbon atoms and containing from 2 to 5 halo substituents as, for example, trifluoromethyl, trichloromethyl or trichloroethyl and the like but, preferably, substituents when the halo groups are fluoro and/or chloro as, for example, trifluoromethyl;

lower alkoxy and lower alkylthio of 1 or 2 carbon atoms as, for example, methoxy or ethoxy;

halo lower alkoxy and halo lower alkylthio of 1 or 2 carbons containing from 3 to 5 halo groups, preferably, fluoro and chloro; typical of these substituents are, for example, trifluoromethoxy, difluorochloromethoxy, trifluoromethoxy, chlorodifluoromethylthio and pentafluoroethoxy;

nitro;

o-phenyl or p-phenyl; and carbalkoxy containing 1 to 4 carbon atoms in the alkoxy moiety. An especially preferred aryl group $R^1$ is phenyl which may optionally contain one or more substituents selected from halo such as chloro, bromo or fluoro, or a nitro, or lower alkyl such as methyl or t-butyl, or phenyl substituent.

Included within this invention are the nontoxic pharmacologically acceptable salts of the products embraced by formula I, supra. The said salts are obtained by treating the products of formula I with a suitable acid such as hydrohalic acids, such as hydrochloric acid and hydrobromic acid, phosphoric acid, nitric acid, and various carboxylic acids such as monocarboxylic acids, dicarboxylic acids and hydroxy substituted carboxylic acids such as acetic acid, maleic acid, succinic acid, fumaric acid, tartaric acid, citric acid, salicyclic acid, sorbic acid and lactic acid, and 1,5-naphthalenedisulphonic acid.

A preferred embodiment of this invention comprises pharmaceutical compositions in which the active ingredient is a triazolyl-O,N-acetal of the formula:

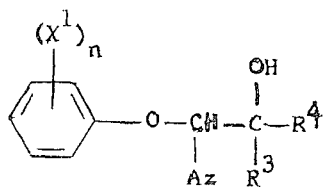

wherein

Az is 1,2,4-triazol-1-yl or 1,2,4-triazol-4-yl;

$R^3$ is hydrogen or lower alkyl;

$R^4$ is lower alkyl, preferably, methyl or t-butyl, or phenyl;

$X^1$ is halo, alkyl, preferably, lower alkyl, nitro or phenyl; and n is an integer having a value of 1–3; and the nontoxic pharmacologically acceptable salts thereof.

A more limited and especially preferred embodiment of this invention comprises those pharmaceutical compositions in which the active ingredient is a compound of the formula:

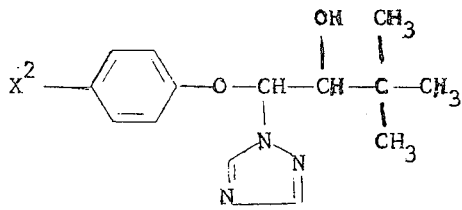

wherein $X^2$ is halo, preferably, chloro, bromo or fluoro, and the nontoxic pharmacologically acceptable salts thereof, preferably, the hydrochlorides.

The compounds of this invention are obtainable both in the erythro-and in the threo-form and are separated in the usual manner as, for example by fractional crystallization or via their tartaric acid salts. However, in most cases they are obtained in the form of racemates. This invention extends to the use of all optical forms, including the said racemates, and any reference in the specification to compounds of the invention are to be construed as embracing all such forms, unless otherwise stated.

The following products fall within the scope of formula I, supra, and are typical of those which may be employed as the active ingredient in the pharmaceutical compositions of this invention:

1-phenoxy-1-[1,2,4-triazol-1-yl]-3,3-dimethyl-2-hydroxybutane (erythro-form), p 1-phenoxy-1-[1,2,4-triazol-1-yl]-3,3-dimethyl-2-hydroxybutane (threo-form), 1-(2'-chlorophenoxy)-1-[1,2,4-triazol-1-yl]-3,3-dimethyl-2-hydroxy-butane, 1-(3'-chlorophenoxy)-1-[1,2,4-triazol-1-yl]-3,3-dimethyl-2-hydroxy-butane, 1-(4'-chlorophenoxy)-1-[1,2,4-triazol-1-yl]-3,3-dimethyl-2-hydroxy-butane, 1-(4'-chlorophenoxy)-1-[1,2,4-triazol-1-yl]-2-hydroxypropane, 1-(4'-chlorophenoxy)-1-[1,2,4-triazol-1-yl]-2-hydroxy-2,3,3-trimethyl-butane, 1-(4'-fluorophenoxy)-1-[1,2,4-triazol-1-yl]-2-hydroxy-3,3-dimethyl-butane, 1-(4'-bromophenoxy)-1-[1,2,4-triazol-1-yl]-2-hydroxy-3,3-dimethyl-butane, 1-(4'-methylphenoxy)-1-[1,2,4-triazol-1-yl]-2-hydroxy-3,3-dimethyl-butane, 1-(4'-diphenoxy)-1-[1,2,4-triazol-1-yl]-2-hydroxy-3,3-dimethyl-butane, 1-(2',4'-dichlorophenoxy)-1-[1,2,4-triazol-1-yl]-2-hydroxy-2,3,3-trimethyl-butane, 1-(2',4'-dichlorophenoxy)-1-[1,2,4-triazol-1-yl]-2-hydroxy-3,3-dimethyl-butane (erythro-form), 1-(2',4'-dichlorophenoxy)-1-[1,2,4-triazol-1-yl]-2-hydroxy-3,3-dimethyl-butane (threo-form), 1-(2',4'-dichlorophenoxy)-1-[1,2,4-triazol-4-yl]-2-hydroxy-3,3-dimethyl-butane, 1-(2'-methyl-4'-chlorophenoxy)-1-[1,2,4-triazol-4-yl]-2-hydroxy-3,3-dimethyl-butane, 1-(3',4'-dimethylphenoxy)-1-[1,2,4-triazol-4-yl]-2-hydroxy-3,3-dimethyl-butane, and 1-(2',4',5'-trichlorophenoxy)-1-[1,2,4-triazol-1-yl]-2-hydroxy-3,3-dimethyl-butane.

The active ingredients of this invention, namely, the triazolyl-O,N-acetals of formula I, supra, are obtained from their corresponding ketone precursors (II, infra) by subjecting the latter to known reduction methods. The following equation illustrates this method of preparation:

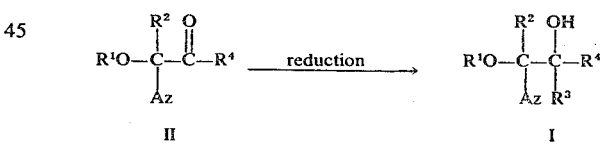

wherein $R^1$, $R^2$, $R^3$, $R^4$ and Az are as defined above. The reduction may be effected by utilizing any one of several known methods. According to one procedure, the ketone starting material (II) is treated with hydrogen in the presence of a catalyst, such as Raney nickel, and in a suitable polar solvent, such as methanol, at 20° to 50°C.

A second reduction method comprises treating the ketone reactant (II) with aluminum isopropylate in the presence of an inert solvent at 20° to 120°C, followed by hydrolysis of the resulting intermediate to afford the desired product.

Still another reductive means consists in treating the ketone precursor (II) with metallic hydride complexes as, for example, with sodium borohydride, in the presence of a polar solvent, such as methanol, at a temperature of 0° to 30°C. The resulting intermediate is then hydrolyzed with an aqueous solution of an acid, such as aqueous hydrochloric acid, to yield the desired triazolyl-O,N-acetal.

Another reductive synthesis consists in treating the said ketone (II) with formamidinesulphinic acid and alkali metal hydroxide as, for example, sodium hydroxide, in aqueous solution at 20° to 100°C in the presence of a polar solvent, such as ethanol.

According to still another procedure, the triazolyl-O,N-acetals can be obtained by subjecting the ketone precursor (II) to reductive alkylation, cycloalkylation, aralkylation or arylation by treatment with Grignard reagents, such as alkyl-, cyclo- alkyl, aralkyl- or arylmagnesium halides as, for example, with the corresponding magnesium iodide or bromide. The process is generally conducted in anhydrous diethyl ether at about 20° to 80°C, followed by the hydrolysis of the resulting intermediate as, for example, by treatment with aqueous ammonium chloride solution. The compounds of this invention thus obtained can be isolated according to customary methods and, if desired, purified, for example by distilling off the solvent if necessary, then extracting the mixture with water and organic solvents, for example ethyl acetate or methylene chloride, and drying the organic phase and freeing it from the solvent. The residue thus obtained is optionally purified by recrystallization or salt formation.

The salts of the instant products (I) are obtained via conventional means by simply treating the latter with the appropriate acid, such as hydrochloric acid, preferably, in a suitable solvent such as an ether as, for example, diethyl ether. In addition to hydrochloric acid other suitable salts include, for example, salts derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid aconitic acid, salicylic acid, phthalic acid, embonic acid, enanthic acid, and the like.

The triazolyl-O,N-acetals (I) display antimicrobial activity and, especially, strong antimycotic activity. They possess a very broad spectrum of antimycotic action, especially against *Dermatophytes* and *Blastomyces* as well as biphase fungi, for example, against species of *Candida*, such as Candida albicans, species of *Epidermophyton* [such as *Epidermophyton floccosum*], species of *Aspergillus* [such as *Aspergillus niger*], species of *Trichophyton* [such as *Trichophyton mentagrophytes*], species of *Microsporon* [such as *Microsporon felineum* ], and species of *Penicillium* [such as *Penicillium commune*]. These microorganisms are not to be interpreted as limitative of the microbes which can be combatted by using the compositions of this invention and are simply illustrative of their character.

By virtue of their pronounced antimicrobial effect, the instant compositions can be used in the treatment of dermatomycoses and systemic mycoses caused by *Trichophyton mentagrophytes* and other species of *Trichophyton*, species of *Microsporon, Epidermophyton floccosum, Blastomyces* and biphase fungi as well as moulds.

The following may also be mentioned as examples of fields of indication in veterinary medicine:

All dermatomycoses and systemic mycoses, especially those caused by the above-mentioned pathogens.

The good antimicrobial activity of the compounds of the invention are demonstrated by the following in vitro and in vivo experiments. 1. Determination of the antimycotic activity in vitro.

Description of the experiment:

The nutrient substrate used was Sabourauds' milieu d'epreuve. The incubation temperature was 28°C and the incubation time was 24 to 96 hours. The test pathogens used were *Candida albicans* and *Trichophyton mentagrophytes* as well as *Aspergillus niger, Coccidioides immitis, Torulopsis glabrata* and other less important pathogens. The tests were carried out with an active compound concentration of 50 γ/ml of nutrient medium.

The test results showed that the compounds of Examples 2,4,5 (threo-form), 8, 12 and 14 (erythro-form and threo-form) completely inhibit the growth of the pathogens both without added serum and on addition of 30% bovine cattle serum. 2. Antimycotic action of the compounds usable according to the invention, in animal experiments. a. Local application in experimental trichophytosis of guinea-pigs (pathogen: *Trichophyton mentagrophytes*):

Description of the experiment:

A 1% strength solution of the active compounds in a dimethylsulphoxide/glycerine/water mixture (1:3:6) or in polyethylene glycol 400 was applied locally for 11 to 14 days after the trichophytosis had been experimentally induced. The experimental results are reproduced in Table A.

Table A

Action of the compounds of the invention on trichophytosis of guinea-pigs:

| Compound of Example No. | Action on *Trichophyton mentagrophytes* |
|---|---|
| 4 | +++ |
| 2 | ++ |

++ reduction of the symptoms of the infection
+++ rapid healing of the infection
++++ complete suppression of symptoms of the infection b. Action on Quinckeanum trichophytosis of white mice, when administered orally:

It was possible to suppress the development of the Quinckeanum infection in mice with doses of 100 mg/kg of body weight, given orally twice daily up the eighth day of infection.

The result can be seen from Table B:

Table B

Action of the compounds of the invention, on Quinckeanum trichophytosis of white mice:

| Compound of Example No. | Oral action on *Trichophyton mentagrophytes* |
|---|---|
| 4 | ++++ |
| 2 | ++++ |
| 11 | +++ |

++ reduction of the symptoms of the infection
+++ rapid healing of the infection
++++ complete suppression of symptoms of the infection c. Candidosis of mice:

Description of the experiment:

Mice of type SPF-CF$_1$ were infected intravenously with 1–2 × 10$^6$ logarithmically growing *Candida* cells which were suspended in physiological sodium chloride solution. One hour before, and seven hours after, the infection, the animals were treated orally with 100 mg of the preparations/kg of body weight.

Untreated animals died of the infection 3 to 6 days after infection. The survival rate on the 6th day after infection was about 5% in the case of untreated control animals.

The experimental results are summarized in Table C:

Table C

Action on candidosis of mice:

| Compound of Example No. | Action on candidosis of mice |
|---|---|
| 4 | +++++ |
| 2 | ++++ |
| 11 | ++ |
| 5 (erythro-form) | +++ |

| +++++ | very good action | = 90% surviving on the 6th day p.i. |
| ++++ | good action | = 80% surviving on the 6th day p.i. |
| +++ | action | = 60–80% surviving on the 6th day p.i. |
| ++ | mild action | = 60% surviving on the 6th day p.i. |

[p.i. = after infection]

The compositions of this invention contain from about 0.1 to about 99.5% and, preferably, 0.5 to 95% of a triazolyl-O,N-acetal (I) as the active ingredient.

In addition, the instant compositions may comprise a combination of two or more of the instant triazolyl-O,N-acetals (I) as the active ingredient or a combination of one or more of said compounds (I) with other pharmacologically active compounds.

The instant compositions are generally employed in dosage unit form, that is in physically discrete units, which contain a specific amount of the drug calculated to produce the desired therapeutic effect. The said dosage units may contain one, two, three, four or more single doses or, alternatively, one-half, a third or fourth of a single dose. Preferably, a single dose contains an amount of active ingredient sufficient to produce the desired therapeutic effect and may be administered once, twice, three or several times a day. The preferred daily dose for administration of the instant medicaments in human application is 500 mg to 30 g and, preferably 2.5 to 30 g of active ingredient.

In general, it is advantageous to administer amounts of active ingredient in concentrations of about 10 to 300 mg/kg and, preferably, 50 to 200 mg/kg of body weight per day to achieve effective results. Nevertheless, it may at times be necessary to deviate from said dosage ranges because of the body weight of the human or animal host to be treated or because of the individual reaction of the said host to the treatment. Other factors which may influence the concentration of active ingredient to be administered include the type of formulation in which the active ingredient is administered, the mode of administration, the point in the progress of the disease being treated and/or the time or intervals of administration. Thus, in some instances it will suffice to use less than the above-mentioned minimum dosage rate, while in other cases the upper limit mentioned must be exceeded to achieve the desired results. Where larger dosages are administered, it may be advisable to divide these into several individual administrations over the course of the day.

The pharmaceutical compositions of this invention contain, in addition to the active ingredient (I), a nontoxic pharmacologically acceptable diluent or carrier which when mixed with the active ingredient renders it more suitable for administration. Examples of solid, liquid and semi-solid diluents and carriers include water, nontoxic organic solvents such as paraffins or petroleum fractions; vegetable oils such as groundnut oil and sesame oil; alcohols such as ethyl alcohol or glycerol; glycols such as propylene glycol or polyethylene glycol; natural rock powders such as kaolins, aluminas, talc or chalk; synthetic rock powders such as highly disperse silica and silicates; sugars such as unrefined sugar, lactose and glucose and the like.

The aforementioned diluents or carriers and any functional equivalents thereof must be adaptable to formulation and serve the following function: a. fillers and extenders, e.g. starch, sugars, mannitol, and silicic acid; b. binding agents, e.g. carboxymethyl cellulose and other cellulose derivatives, alginates, gelatine and polyvinyl pyrrolidone; c. moisturizing agents, e.g. glycerol; d. disintegrating agents, e.g. agar-agar, calcium carbonate and sodium bicarbonate; e. agents for retarding dissolution e.g. paraffin; f. resorption accelerators, e.g. quaternary ammonium compounds; g. surface active agents, e.g. cetyl alcohol, glycerol monostearate; h. adsorptive carriers, e.g. kaolin and bentonite; i. lubricants, e.g. talc, calcium and magnesium stearate and solid polyethylene glycols.

The compositions of this invention are administered parenterally or orally in any of the usual pharmaceutical forms. These include solid and liquid oral unit dosage forms such as tablets, capsules, powders, suspensions, solutions, syrups and the like including sustained release preparations and fluid injectable forms such as sterile solutions and suspensions.

Powders and sprays are prepared by comminuting the compound to a suitably fine size and mixing with a similarly comminuted diluent pharmaceutical carrier as, for example, lactose, talc, silicic acid, aluminum hydroxide, calcium silicate and polyamide powder or mixtures of these substances. Aerosol sprays may, for example, contain the usual propellants, for example, chlorofluorohydrocarbons. Sweetening, flavoring, preservative, dispersing and coloring agents can also be present.

Pharmaceutical compositions adapted for topical administration include ointments, solutions, lotions, creams, pastes and gels and the like. Said compositions may contain as diluents, for example, animal and vegetable fats, waxes, paraffins, starch, tragacanth, cellulose derivatives, polyethylene glycols, silicones, bentonites, silicic acid, talc and zinc oxide or mixtures of same. One suitable composition includes, for example, a 1 wt.% solution of the compound in polyethylene glycol 400.

Oral administration can be effected utilizing solid and liquid dosage unit forms such as powders, tablets, dragees, capsules, granulates, suspensions, solutions and the like.

Solutions, syrups, emulsions and elixirs can be prepared in dosage unit form so that a given quantity contains a predetermined amount of the active ingredient. Syrups are prepared by dissolving the said active ingredient in a suitably flavored aqueous sucrose solution while elixirs are prepared through the use of a nontoxic alcoholic vehicle. Suspensions are formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin and the like can also be added. When, for example, the compositions are solutions and emulsions the diluents include water, ethyl alcohol, isopropyl alcohol, ethyl carbonate, ethyl acetate, benzyl alcohol, benzyl benzoate, propylene glycol, 1,3-butylene glycol, dimethylformamide, oils such as groundnut oil, glycerol, tetrahydrofurfuryl alcohol, polyethylene glycols and fatty acid esters of sorbitol or mixtures thereof.

Tablets are formulated by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Capsules are prepared by comminuting the active ingredient to a suitably fine size and mixing with a similarly comminuted pharmaceutical carrier such as an edible carbohydrate as, for example, starch, lactose, sucrose, glucose or mannitol. The powdered mixture can then be poured into gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets, dragees, capsules and pills formed from the pharmaceutical compositions of this invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or wax.

Rectal administration can be effected utilizing suppositories in which the compound is admixed with low melting water soluble or insoluble solids such as polyethylene glycol, cocoa butter, higher esters as, for example myristyl palmitate, or mixtures thereof.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Although the instant compositions can be administered perorally, parenterally (for example intramuscularly, intraperitoneally or intravenously), rectally or topically, it is preferred that administration be effected orally or topically. Preferred pharmaceutical compositions therefore comprise those which are adapted for peroral and topical administration, such as tablets, capsules containing measured doses of the active ingredient, ointments, and lotions.

The following Examples 1–28 illustrate the preparation of compounds which may be used as the active ingredient in the compositions of this invention. All the compounds of the invention can be prepared by these or by analogous methods.

EXAMPLE 1

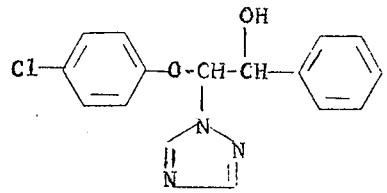

31.4 g (0.1 mol) of ω-[4'-chlorophenoxy]-ω-[1,2,4-triazol-1'-yl]-acetophenone are dissolved in 300 ml of methanol and 3 g (0.08 mol) of sodium borohydride are introduced into the solution while stirring and cooling with ice. The reaction mixture is stirred for 1 hour at room temperature and the solvent is then distilled off in vacuo.

The residue is taken up in dilute hydrochloric acid and the mixture is briefly heated and filtered. The filtrate is rendered alkaline with sodium hydroxide solution. The precipitate thereby produced is filtered off and taken up in ethyl acetate. After distilling off the ethyl acetate, an oil remains, which crystallizes on trituration with ligroin.

After recrystallization from ligroin/isopropanol, 25 g (98% of theory) of 1-(4'-chlorophenoxy)-1-[1,2,4-triazol-1'-yl]-2-phenyl-ethanol of melting point 117°C is obtained.

EXAMPLE 2

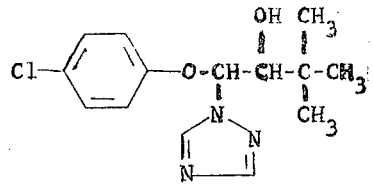

587 g (2 mols) of 1-(4'-chlorophenoxy)-1-[1,2,4-triazol-1'-yl]-3,3-dimethyl-butan-2-one are dissolved in 3 liters of methanol. 80 g (2 mols of sodium borohydride are added thereto in portions of 5 g at 0 to 10°C while stirring and cooling with ice, and the mixture is stirred for 2 hours at 5 to 10°C and then for 12 hours at room temperature.

The mixture is then cooled to 10°C and 300 g (3 mols) of concentrated aqueous hydrochloric acid are added at 10° to 20°C. After stirring for 6 hours at room temperature, the suspension obtained is diluted with 3.8 liters of water which contains 400 g (4.8 mols) of sodium bicarbonate. The precipitate thereby produced is filtered off to afford 502 g (85% of theory) of 1-(4'-chlorophenoxy)-1-[1,2,4-triazol-1'-yl]-2-hydroxy-3,3-dimethyl-butane having a melting point of 112°–117°C.

EXAMPLE 3

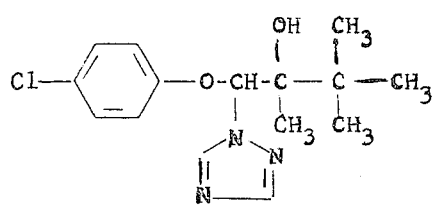

A solution of 31.2 g (0.22 mol) of methyl iodide in 100 ml of anhydrous ether is added dropwise to a suspension of 4.8 g (0.22 mol) of magnesium filings in 50 ml of anhydrous ether while stirring and using reflux cooling, the solvent coming to the boil during the addition. After completion of the addition, a solution of 29.4 g (0.1 mol) of 1-(4'-chlorophenoxy)-1-[1,2,4-triazol-1'-yl]-3,3-dimethyl-butan-2-one in 100 ml of anhydrous ether is added dropwise to this Grignard solution and the mixture is heated to boiling under reflux for 18 hours.

After cooling, the reaction mixture is introduced into a solution of 80 g of ammonium chloride in 600 ml of water, 250 ml of ethyl acetate are added thereto and the mixture is stirred for 15 minutes. The organic phase is separated off and the aqueous phase is again extracted with ethyl acetate. Both the ethyl acetate extracts are washed twice with 100 ml of water at a time, dried over sodium sulphate and freed of the solvent in vacuo. The crystalline precipitate is taken up in hot petroleum ether, which leaves it undissolved, and the product is filtered off hot to afford 11 g (36% of theory) of 1-(4'-chlorophenoxy)-1-[1,2,4-triazol-1'-yl]-2-hydroxy-2,3,3-trimethyl-butane having a melting point of 158°–160°C.

EXAMPLE 4

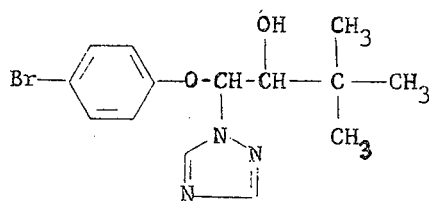

33.6 g (0.1 mol) of 1-(4'-bromophenoxy-1-[1,2,4-triazol-1'-yl]-3,3-dimethyl-butan-2-one are dissolved in 300 ml of ethanol and a sodium hydroxide solution containing 8 g (0.2 mol) of sodium hydroxide in 40 ml of water is added thereto, followed by 32.4 g (0.3 mol) of formamidinesulphinic acid. The reaction mixture is heated to boiling for 3 hours under reflux and filtered and the solvent is then distilled off in vacuo.

The oily residue is taken up in 100 ml of water and extracted twice with 100 ml portions of methylene chloride. The combined organic phases are washed twice with 100 ml of water, dried over sodium sulphate and the solvent is evaporated in vacuo.

The resulting oil is boiled with petroleum ether, whereupon it crystallizes and the resulting product is filtered to afford 26.5 g (79% of theory) of 1-(4'-bromophenoxy)-1-[1,2,4-triazol-1'-yl]-2-hydroxy-3,3-dimethyl-butane having a melting point of 115°–118°C.

EXAMPLE 5

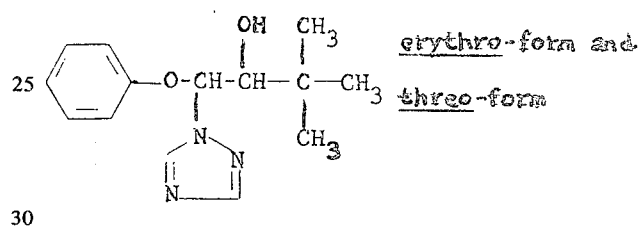

29.5 g (0.114 mol) of 1-phenoxy-1-[1,2,4-triazol-1'-yl]-3,3-dimethyl-butan-2-one are dissolved in 250 ml of methanol and 5.8 g (0.15 mol) of sodium borohydride is added thereto in portions at 0° to 5°C, with stirring and reflux cooling. After subsequently stirring for 12 hours at room temperature, the mixture is worked up according to the procedure described in Example 2 using 20 ml of concentrated hydrochloric acid and 250 ml of saturated sodium bicarbonate solution. The resulting suspension containing sodium bicarbonate is twice extracted with 150 ml portions of methylene chloride and the combined organic extracts are washed twice with 100 ml of water until neutral and then dried and freed from the solvent in vacuo. The resulting oil is boiled up with hot petroleum ether. A crystalline residue (A) is thus obtained, which is filtered off hot, and dried. The filtrate is freed from the solvent in vacuo and this residue (B) is triturated with petroleum ether and a little ether.

A total (A + B) of 23.4 g (79% of theory) of 1-phenoxy-1-[1,2,4-triazol-1'-yl]-2-hydroxy-3,3-dimethyl-butane is obtained, including 4.1 g (A) of the erythro-form of melting point 132°C and 19.3 g (B) of the threo-form of melting point 88°–94°C.

By following the procedure described in Examples 1, 2, 4 and 5 but substituting the appropriate starting material for those recited therein, those compounds of formula I wherein $R^3$ represents hydrogen may be obtained. The following equation illustrates the process of Examples 1, 2, 4 and 5 and together with Table I illustrates the starting materials (IIa) employed and the compounds (Ia) obtained thereby:

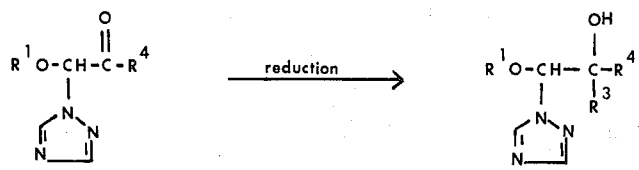
TABLE I
| Example | R¹ | R³ | R⁴ | Melting point (°C) |
|---|---|---|---|---|
| 6 | $O_2N$—⟨phenyl⟩— | H | $C(CH_3)_3$ | 194–196 |
| 7 | $(CH_3)_3C$—⟨phenyl⟩— | H | $C(CH_3)_3$ | 113–117 |
| 8 | $H_3C$—⟨phenyl⟩— | H | $C(CH_3)_3$ | 123–127 |
| 9 | 2-Cl-⟨phenyl⟩— | H | $C(CH_3)_3$ | 107–112 |
| 10 | 3-Cl-⟨phenyl⟩— | H | $C(CH_3)_3$ | 114–115 |
| 11 | F—⟨phenyl⟩— | H | $C(CH_3)_3$ | 99–110 |
| 12 | biphenyl-4-yl | H | $C(CH_3)_3$ | 98–100 |
| 13 | biphenyl-2-yl | H | $C(CH_3)_3$ | threo-form: 115–117<br>erythro-form: 186–190 |
| 14 | 3,4-Cl₂-⟨phenyl⟩— | H | $C(CH_3)_3$ | threo-form: 114–116<br>erythro-form: 161–164 |
| 15 | 4-Cl-2-CH₃-⟨phenyl⟩— | H | $C(CH_3)_3$ | 107–110 |

-continued

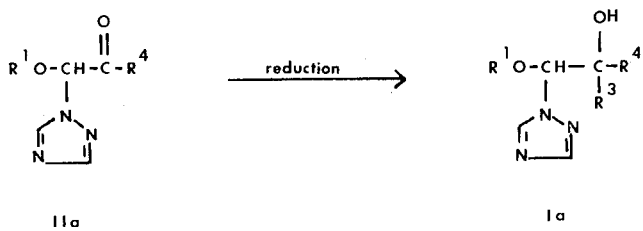

IIa → Ia

TABLE I

| Example | R¹ | R³ | R⁴ | Melting point (°C) |
|---|---|---|---|---|
| 16 | 2,3-dimethylphenyl | H | C(CH₃)₃ | 133–135 |
| 17 | 2,4,5-trichlorophenyl | H | C(CH₃)₃ | 137–144 |

IIa → Ia

| Example | R¹ | R² | R³ | R⁴ | Az | Melting point (°C) |
|---|---|---|---|---|---|---|
| 18 | 3,4-dichlorophenyl | H | H | C(CH₃)₃ | 1,2,4-triazol-1-yl | 185–187 |
| 19 | 4-chlorophenyl | H | H | CH₃ | 1,2,4-triazol-1-yl | 84–90 |
| 20 | 4-(methoxycarbonyl)phenyl | H | H | C(CH₃)₃ | 1,2,4-triazol-1-yl | 136–38 |
| 21 | 4-cyclohexylphenyl | H | H | C(CH₃)₃ | 1,2,4-triazol-1-yl | 115–120 |
| 22 | 3-chlorobiphenyl-4-yl | H | H | C(CH₃)₃ | 1,2,4-triazol-1-yl | 95–8 |
| 23 | 2-cyclohexylphenyl | H | H | C(CH₃)₃ | 1,2,4-triazol-1-yl | 92–5 |

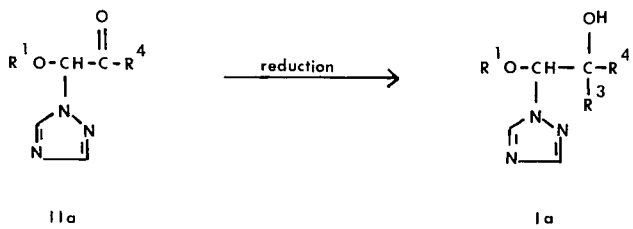

IIa            Ia

TABLE I

| Example | $R^1$ | $R^2$ | $R^3$ | $R^4$ | Az | Melting point (°C) |
|---|---|---|---|---|---|---|
| 24 | 3,4-dichlorobiphenyl | H | H | $C(CH_3)_3$ | 1,2,4-triazol-1-yl | 142–44 |

The Grignard reaction of Example 3 may also be used to synthesize products wherein $R^3$ in formula I is hydrogen; however, this process is also suitable for preparing products wherein $R^3$ is other than hydrogen. The following equation illustrates the process of Example 3 and together with Table II illustrates the starting materials (II) employed and the compounds (I) obtained thereby:

late compositions comprising all of the compounds (I) described in this specification:

EXAMPLE 28

1% Strength solution for topical treatment:

Sufficient polyethylene glycol 400 is added to 1 g of 1-(4'-bromophenoxy)-1-[1,2,4-triazol-1'-yl]-2-hydroxy-3,3-dimethyl-butane while stirring and warming gently, to give a total of 100 g of solution.

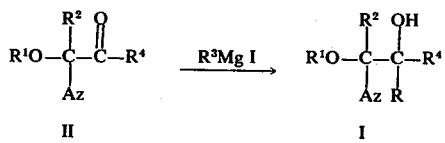

II         I

TABLE II

| Example | $R^1$ | $R^2$ | $R^3$ | $R^4$ | Az | Melting point (°C) |
|---|---|---|---|---|---|---|
| | 2,4-dichlorophenyl | H | $CH_3$ | $C(CH_3)_3$ | 1,2,4-triazol-1-yl | 101–103 |
| | 4-chlorophenyl | H | $CH_2$-phenyl | $C(CH_3)_3$ | 1,2,4-triazol-1-yl | 113–116 |
| | 4-chlorophenyl | H | $CH_3$ | phenyl | 1,2,4-triazol-1-yl | 171–73 |

The following examples illustrate pharmaceutical compositions and a medicament in dosage unit form formulated according to this invention. The preparative methods in these examples can be used to formu-

EXAMPLE 29

1% Strength ointment for topical treatment:

1 g of 1-(4'-bromophenoxy)-1-[1,2,4-triazol-1'-yl]-2-hydroxy-3,3-dimethyl-butane is ground with 5 g of viscous paraffin oil. Thereafter, sufficient ointment base of paraffin oil and polyethylene is added to give a total of 100 g of ointment.

EXAMPLE 30

10% Strength suspension syrup for oral administration:

Sufficient vegetable oil is added to a mixture of 10 g of 1-(4'-chlorophenoxy)-1-[1,2,4-triazol-1'-yl]-2-hydroxy-3,3-dimethyl-butane, 0.05 g of sodium saccharin, 2g of colloidal silica and 0.2 g of peppermint oil to give a total of 100 g of suspension syrup.

EXAMPLE 31

Tablets containing 200 mg of active compound, for oral administration:

2g of 1-(4'-bromophenoxy)-1-[1,2,4-triazol-1'-yl]-2-hydroxy-3,3-dimethyl-butane, 1 g of lactose and 0.3 g of corn starch are granulated with 0.1 of corn starch paste. The mixture is beaten through a sieve of about 4–6 mm mesh width and is dried. This dried mixture is homogenized by passing it through a sieve of 0.8 to 1 mm mesh width and is then mixed with 0.15 g of starch and 0.02 g of magnesium stearate. The mixture thus obtained is pressed to give 10 tablets.

What is claimed is:

1. A pharmaceutical composition for treating mycotic infections in humans and animals which comprises an antimycotally effective amount of a compound of the formula

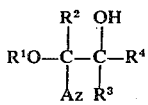

or a pharmaceutically acceptable nontoxic salt thereof, wherein
$R^1$ is phenyl unsubstituted or substituted by chloro, bromo, fluoro, dichloro or trichloro;
$R^2$ is hydrogen;
$R^3$ is hydrogen or lower alkyl;
$R^4$ is lower alkyl; and
Az is 1,2,4-triazol-1-yl or 1,2,4-triazol-4-yl unsubstituted or substituted by 1 or 2 substituents selected from the group consisting of halo and lower alkyl; in combination with a pharmaceutically acceptable nontoxic inert diluent or carrier.

2. A composition according to claim 1 in which the compound is of the formula:

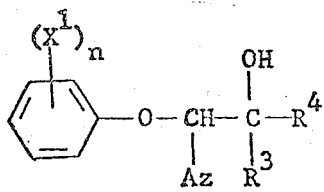

or a pharmaceutically acceptable nontoxic salt thereof, wherein
Az is 1,2,4,-triazol-1-yl or 1,2,4-triazol-4-yl;
$R^3$ is hydrogen or lower alkyl;
$R^4$ is lower alkyl;
$X^1$ is halo; and
n is an integer having a value of 1-3.

3. A composition according to claim 2 wherein $R^4$ is methyl or t-butyl.

4. A composition according to claim 1 in which the compound is of the formula:

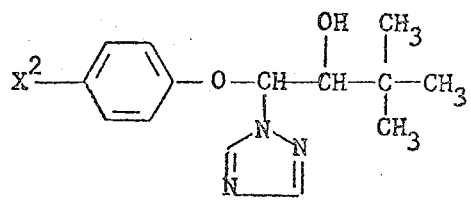

or a pharmaceutically acceptable nontoxic salt thereof, wherein $X^2$ is halo.

5. A composition according to claim 4 wherein $X^2$ is chloro, bromo or fluoro.

6. A composition according to claim 1 wherein Az is

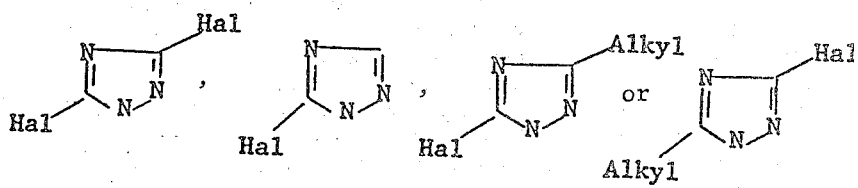

wherein Hal is chloro or bromo and Alkyl is an alkyl moiety of 1 to 4 carbon atoms.

7. A composition according to claim 6 wherein the alkyl moiety is methyl.

8. A composition according to claim 1 wherein the compound is 1-(4'-chlorophenoxy)-1-[1,2,4-triazol-1'-yl]-2-hydroxy-2,3,3-trimethyl-butane.

9. A composition according to claim 1 wherein the compound is the erythro- or threo-form of 1-phenoxy-1-[1,2,4-triazol-1-yl]-3,3-dimethyl-2-hydroxy-butane.

10. A composition according to claim 1 wherein the compound is 1-(2'-chlorophenoxy)-1-[1,2,4-triazol-1'-yl]-3,3-dimethyl-2-hydroxy-butane.

11. A composition according to claim 1 wherein the compound is 1-(3'-chlorophenoxy)-1-[1,2,4-triazol-1'-yl]-3,3-dimethyl-2-hydroxy-butane.

12. A composition according to claim 1 wherein the compound is 1-(4'-chlorophenoxy)-1-[1,2,4-triazol-1'-yl]-3,3-dimethyl-2-hydroxy-butane.

13. A composition according to claim 1 wherein the compound is 1-(4'-chlorophenoxy)-1-[1,2,4-triazol-1'-yl]-2-hydroxy-propane.

14. A composition according to claim 1 wherein the compound is 1-(4'-fluorophenoxy)-1-[1,2,4-triazol-1'-yl]-2-hydroxy-3,3-dimethyl-butane.

15. A composition according to claim 1 wherein the compound is 1-(4'-bromophenoxy)-1-[1,2,4-triazol-1'-yl]-2-hydroxy-3,3-dimethyl-butane.

16. A composition according to claim 1 wherein the compound is 1-(2',4'-dichlorophenoxy)-1-[1,2,4-triazol-1'-yl]-2-hydroxy-2,3,3-trimethyl-butane.

17. A composition according to claim 1 wherein the compound is the erythro- or threo-form of 1-(2',4'-dichlorophenoxy)-1-[1,2,4-triazol-1'-yl]-2-hydroxy- 3,3-dimethyl-butane.

18. A composition according to claim 1 wherein the compound is 1-(2',4'-dichlorophenoxy)-1-[1,2,4-triazol-4'-yl]-2-hydroxy-3,3-dimethyl-butane.

19. A composition according to claim 1 wherein the compound is 1-(2',4',5'-trichlorophenoxy)-1-[1,2,4-triazol-1'-yl]-2-hydroxy-3,3-dimethyl-butane.

20. A composition according to claim 1 wherein
R$^1$ is phenyl unsubstituted or substituted by chloro, bromo, or trichloro;
R$^2$ is hydrogen;
R$^3$ is hydrogen or methyl;
R$^4$ is methyl or t-butyl; and
Az is 1,2,4-triazol-1'-yl or 1,2,4-triazol-4'-yl.

21. A method of treating mycotic infections in humans and animals which comprises administering to such human or animal an antimycotically effective amount of a compound of the formula:

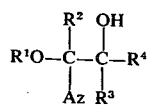

or a pharmaceutically acceptable nontoxic salt thereof, wherein
R$^1$ is phenyl unsubstituted or substituted by chloro, bromo, fluoro, dichloro or trichloro;
R$^2$ is hydrogen;
R$^3$ is hydrogen or lower alkyl;
R$^4$ is lower alkyl; and
Az is 1,2,4-triazol-1-yl, 1,2,4-triazol-4-yl or 1,2,3-triazol-1-yl unsubstituted or substituted by 1 or 2 substituents selected from the group consisting of halo and lower alkyl;
in combination with a pharmaceutically acceptable nontoxic inert diluent or carrier.

22. A method according to claim 21 wherein the compound is of the formula:

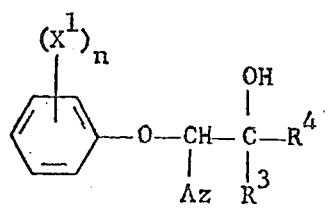

or a pharmaceutically acceptable nontoxic salt thereof, wherein
Az is 1,2,4-triazol-1-yl or 1,2,4-triazol-4-yl;
R$^3$ is hydrogen or lower alkyl;
R$^4$ is lower alkyl;
X$^1$ is halo; and
n is an integer having a value of 1-3.

23. A method according to claim 22 wherein R$^4$ is methyl, t-butyl or phenyl.

24. A method according to claim 21 wherein the compound is of the formula:

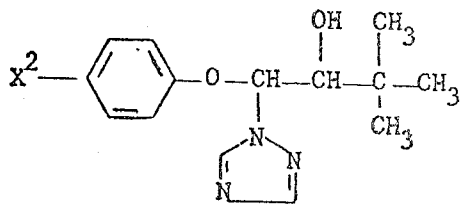

or a pharmaceutically acceptable nontoxic salt thereof, wherein
X$^2$ is halo.

25. A method according to claim 24 wherein X$^2$ is chloro, bromo or fluoro.

26. A method according to claim 21 wherein Az is

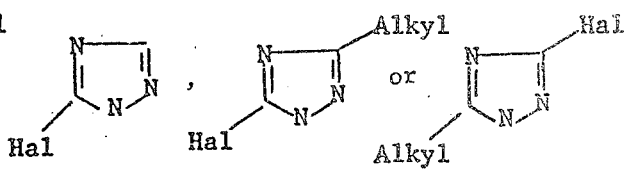

wherein
Hal is chloro or bromo and
Alkyl is an alkyl moiety of 1 to 4 carbon atoms.

27. A method according to claim 26 wherein the alkyl moiety is methyl.

28. A method according to claim 21 wherein
R$^1$ is phenyl unsubstituted or substituted by chloro, bromo, fluoro, or trichloro;
R$^2$ is hydrogen;
R$^3$ is hydrogen or methyl;
R$^4$ is methyl or t-butyl; and
Az is 1,2,4-triazol-1'yl or 1,2,4-triazol-4'-yl.

29. A method according to claim 21 wherein the compound is 1-(4'-chlorophenoxy)-1-[1,2,4-triazol-1'-yl]-2-hydroxy-2,3,3-trimethyl-butane.

30. A method according to claim 21 wherein the compound is the erythro- or threo-form of 1-phenoxy-1-[1,2,4-triazol-1'-yl]-3,3-dimethyl-2-hydroxy-butane.

31. A method according to claim 21 wherein the compound is 1-(2'-chlorophenoxy)-1-[1,2,4-triazol-1'-yl]-3,3-dimethyl-2-hydroxy-butane.

32. A method according to claim 21 wherein the compound is 1-(3'-chlorophenoxy)-1-[1,2,4-triazol-1'-yl]-3,3-dimethyl-2-hydroxy-butane.

33. A method according to claim 21 wherein the compound is 1-(4'-chlorophenoxy)-1-[1,2,4-triazol-1'-yl]-3,3-dimethyl-2-hydroxy-butane.

34. A method according to claim 21 wherein the compound is 1-(4'-chlorophenoxy)-1-[1,2,4-triazol-1'-yl]-2-hydroxy-propane.

35. A method according to claim 21 wherein the compound is 1-(4'-fluorophenoxy)-1-[1,2,4-triazol-1'-yl]-2-hydroxy-3,3-dimethyl-butane.

36. A method according to claim 21 wherein the compound is 1-(4'-bromophenoxy)-1-[1,2,4-triazol-1'-yl]-2-hydroxy-3,3-dimethyl-butane.

37. A method according to claim 21 wherein the compound is 1-(2',4'-dichlorophenoxy)-1-[1,2,4-triazol-1'-yl]-2-hydroxy-2,3,3-trimethyl-butane.

38. A method according to claim 21 wherein the compound is the erythro- or threo-form of 1-(2',4'-dichlorophenoxy)-1-[1,2,4-triazol-1'-yl]-2-hydroxy-3,3-dimethyl-butane.

39. A method according to claim 21 wherein the compound is 1-(2',4',5'-trichlorophenoxy)-1-[1,2,4-triazol-1'-yl]-2-hydroxy-3,3-dimethyl-butane.

* * * * *